United States Patent [19]

Tomas

[11] Patent Number: 5,674,539
[45] Date of Patent: Oct. 7, 1997

[54] METHOD OF TREATING SKIN AND COMPOSITION

[76] Inventor: Robert E. Tomas, 29926 S. Stockton, Farmington Hills, Mich. 48336

[21] Appl. No.: 505,722

[22] Filed: May 18, 1995

Related U.S. Application Data

[63] Continuation-in-part of Ser. No. 352,363, Dec. 9, 1994, abandoned.

[51] Int. Cl.⁶ .......................... A61K 31/65; A61K 33/04
[52] U.S. Cl. ................. 424/702; 424/705; 424/713; 514/152; 514/154; 514/859
[58] Field of Search ........................ 514/152, 154, 514/859; 424/702, 705, 713

[56] References Cited

U.S. PATENT DOCUMENTS

| | | | |
|---|---|---|---|
| 1,860,320 | 5/1932 | Nordlander | 424/702 |
| 3,152,046 | 10/1964 | Kapral | 167/87 |
| 4,005,198 | 1/1977 | Skillern | 424/227 |
| 4,505,896 | 3/1985 | Bernstein | 424/164 |
| 4,885,157 | 12/1989 | Flaschetti | 424/59 |
| 5,151,209 | 9/1992 | McCall | 252/174 |
| 5,258,183 | 11/1993 | Grimberg | 424/401 |
| 5,332,577 | 7/1994 | Gertner et al. | 424/449 |
| 5,385,938 | 1/1995 | Yu et al. | 514/557 |

*Primary Examiner*—Allen J. Robinson
*Attorney, Agent, or Firm*—Alvin S. Blum

[57] ABSTRACT

A topical medication for the treatment of skin pathology including acne is comprised of tetracycline, minocycline, clindamycin, erythromycin, or doxicycline and selenium sulfide or sulfur in a pharmaceutically acceptable carrier. The lotion, cream or ointment is applied to the lesions, left in place briefly and washed off. This is repeated twice daily. The lesions generally clear up within a week. Because the treatment is local, the serious side effects of systemic administration of drugs is avoided.

10 Claims, No Drawings

METHOD OF TREATING SKIN AND COMPOSITION

This application is a continuation-in-part of application Ser. No. 08/352,363, filed Dec. 9, 1994, now abandoned.

FIELD OF THE INVENTION

This invention relates to the use of tetracycline in combination with sulfur or selenium sulfide in topical preparations for the treatment of acne.

BACKGROUND OF THE INVENTION

The treatment of acne vulgaris has been directed primarily to cleansing the skin, avoidance of certain foods and chocolate and the topical application of various astringents and ointments. Certain chemicals have been tried with variable success including peroxides topically applied. A theory has developed that a causative factor may be the formation of free fatty acids in the sebaceous glands or ducts.

U.S. Pat. No. 4,005,198 issued Jan. 25, 1977 to Skillern discloses the use of the specific duiretic Methyclothiazide orally in conjunction with oral tetracycline to control acne with the tetracycline discontinued after some reduction in symptoms. The antibiotic is used in this case for its purported action in reducing the formation of free fatty acids in the sebaceous ducts and not for its antibiotic activity.

In contrast to topical application, systemic administration to treat localized skin lesions subjects the rest of the body to all of the dangerous side effects while presenting only low concentrations of drug to the areas to be treated.

SUMMARY OF THE INVENTION

It is accordingly an object of the invention to provide an effective topical composition that will be effective in treating acne vulgaris, cystic type lesions, folliculitis and other skin pathology, while having negligible effects on the rest of the body.

Applicant has discovered that a preparation incorporating tetracycline, minocycline, clindamycin, erythromycin, or doxicycline in combination with either selenium sulfide or elemental sulfur in a pharmaceutically acceptable carrier, when applied periodically to the skin lesions for only brief contact intervals, is most effective in causing a marked improvement in the condition promptly without systemic side effects.

DETAILED DESCRIPTIONS OF PREFERRED EMBODIMENTS

In the practice of the present invention, tetracyline hydrochloride, minocycline, clindamycin, erythromycin, or doxicycline is distributed with either selenium sulfide or elemental sulfur in various pharmaceutically acceptable carriers such as lotions, creams and ointments for topical applications to the skin by techniques well known in the art. Some of these carriers may contain diluents such as alcohols, glycols and the like as well as suspending, wetting, and emulsifying agents, as desired.

The compositions of the instant invention and the methods of their use will be more readily comprehended from the following examples and clinical tests.

EXAMPLES

Example I 1.8 grams of tetracyline hydrochloride suspended in 60 c.c. of an aqueous suspension of 2.5% selenium sulfide containing suitable carrier materials including bentonite.

Example II 30 grams elemental sulfur powder
1.5 grams tetracyline hydrochloride suspended in 30 grams 70% isopropyl alcohol

Test A 26 year old white male with superficial papular and pustular facial acne tested positive for Staphylococcus Aureus.
Oral tetracyline 250 mg BID cleared skin but caused diarrhea required cessation of treatment.
Acne returned.
Example I rubbed into lesions, twice a day, and washed away 5 minutes later.
Acne resolved within six days.

Test B 28 year old white male with papular and cystic lesions on back.
Applied example I to affected areas, washed off after 5 minutes.
Treated twice a day.
Acne resolved in 4 days.

Test C 26 year old white male with superficial papular and pustular facial lesions.
Rubbed example II into lesions twice a day, washed off after 5 minutes.
Lesions cleared in four days.

Test D 42 year old white female with mild cystic and pustular facial acne.
Treated twice a day with example II, washing off after 5 minutes.
Acne cleared in seven days.

It is apparent that the preparations of the invention exert a healing action on all of the various inflamed and affected parts of the skin in various skin pathologies.

Because of the brief topical mode of application the dose and concentration of ingredients are not critical. The antibiotic component of the mixture, i.e., the tetracycline, minocycline, clindamycin, erythromycin, or doxicycline may be present in a concentration range of from about ½ gram to about 7 grams per 100 c.c. The selenium sulfide may be present in a concentration range of from about ½ gram to about 7 grams per 100 c.c. The sulfur may be present in a concentration range of from about ½ gram to about 120 grams per 100 c.c.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

What is claimed is:

1. A method for the topical treatment of acne lesions in a patient having acne comprising topically applying a therapeutically effective amount of a combination of an antibiotic selected from the group consisting of minocycline, doxicycline, and tetracycline and a therapeutically effective amount of an agent selected from the group consisting of selenium sulfide and sulfur in a pharmaceutically acceptable non-solid carrier directly onto said lesions, and in which said combination is applied and then removed after a time interval of less than an hour at least twice per day.

2. A therapeutic composition for the topical treatment of acne lesions by direct application to said lesions, said composition comprising in combination:

a therapeutically effective amount of an antibiotic selected from the group consisting of minocycline, doxicycline, and tetracycline;

a therapeutically effective amount of selenium sulfide; and a pharmaceutically acceptable non-solid carrier.

3. The composition according to claim 2, in which said carrier forms a cream.

4. The composition according to claim 2, in which said carrier forms a lotion.

5. The composition according to claim 2, in which said carrier forms an ointment.

6. The composition according to claim 2, in which said antibiotic is tetracycline.

7. The composition according to claim 2, in which said antibiotic is minocycline.

8. The composition according to claim 2, in which said antibiotic is doxicycline.

9. A therapeutic composition for the topical treatment of skin pathology by direct application to the affected tissue comprising in combination therapeutically effective amounts of:

at least one antibiotic selected from the group consisting of minocycline, clindamycin, erythromycin, and doxicycline;

at least one agent selected from the group consisting of selenium sulfide and sulfur; and a pharmaceutically acceptable carrier for providing said combination in a form selected from the group consisting of lotion, cream and ointment.

10. A therapeutic composition for the topical treatment of acne lesions by direct application to said lesions, the composition consisting essentially of, in combination:

a therapeutically effective amount of at least one antibiotic selected from the group consisting of minocycline, doxicycline, and tetracycline;

a therapeutically effective amount of at least one agent selected from the group consisting of selenium sulfide and sulfur; and a pharmaceutically acceptable carrier.

\* \* \* \* \*